US007599159B2

(12) United States Patent
Feese et al.

(10) Patent No.: US 7,599,159 B2
(45) Date of Patent: Oct. 6, 2009

(54) VOLTAGE-RESISTANT MOS SWITCH

(75) Inventors: Ulrich Feese, Berlin (DE); Robert Kessler, Berlin (DE); Michael Wrana, Berlin (DE)

(73) Assignee: Biotronik GmbH & Co. KG (DE)

( * ) Notice: Subject to any disclaimer, the term of this patent is extended or adjusted under 35 U.S.C. 154(b) by 272 days.

(21) Appl. No.: 10/933,816

(22) Filed: Sep. 3, 2004

(65) Prior Publication Data

US 2005/0052806 A1    Mar. 10, 2005

(30) Foreign Application Priority Data

Sep. 5, 2003    (DE) ................ 103 41 940
Dec. 5, 2003    (DE) ................ 103 58 048

(51) Int. Cl.
*H02H 3/20*    (2006.01)
*H02H 9/04*    (2006.01)

(52) U.S. Cl. .................. 361/56; 361/91.1; 361/111

(58) Field of Classification Search ............ 361/91.1, 361/56, 111

See application file for complete search history.

(56) References Cited

U.S. PATENT DOCUMENTS

| 4,487,457 | A |   | 12/1984 | Janutka ............... 327/404 |
| 4,864,126 | A |   | 9/1989 | Walters et al. ........... 250/551 |
| 5,095,224 | A | * | 3/1992 | Renger ................ 327/110 |
| 5,148,064 | A |   | 9/1992 | Kevorkian et al. ........ 307/571 |
| 5,563,759 | A | * | 10/1996 | Nadd .................. 361/101 |
| 5,574,385 | A | * | 11/1996 | Murphy et al. .......... 324/765 |
| 5,877,619 | A | * | 3/1999 | Keller ............... 324/76.11 |
| 6,473,649 | B1 | * | 10/2002 | Gryzwa et al. ........... 607/28 |
| 6,529,777 | B1 | * | 3/2003 | Holmstrom et al. ...... 607/119 |
| 2003/0016072 | A1 |   | 1/2003 | Ramakrishnan .......... 327/434 |

FOREIGN PATENT DOCUMENTS

| DE | 3534861 | * | 9/1985 | ............... 327/434 |
| DE | 35 34 861 |   | 4/1987 | |
| DE | 37 35 511 |   | 5/1988 | |

(Continued)

OTHER PUBLICATIONS

"Interrupteur A 5 Mosfet Serie 2000 V/15A," Electronique, CEP Communications (Paris, France), Nr. 3, p. 56-58, 60, XP000177309 Issue 1157-1152(Dec. 12, 1990).

*Primary Examiner*—Stephen W Jackson
*Assistant Examiner*—Zeev Kitov
(74) *Attorney, Agent, or Firm*—Hahn Loeser & Parks LLP

(57) ABSTRACT

A voltage-resistant switch comprising a first switching contact and a second switching contact, and an MOS switching transistor having a source terminal, a drain terminal and a gate terminal, wherein the source terminal of the MOS switching transistor is connected to the second switching contact, and the drain terminal of the MOS switching transistor is connected to the first switching contact. The voltage-resistant switch has a switching monitoring unit with a control input and a protection output and a protection switch with a switching input, wherein the switching input is connected to the protection output of the switching monitoring unit and the protection switch is arranged and adapted to electrically connect the gate terminal of the first MOS switching transistor to the source terminal of the first MOS switching transistor in dependence on a protection signal.

15 Claims, 4 Drawing Sheets

FOREIGN PATENT DOCUMENTS

| | | | |
|---|---|---|---|
| DE | 512605 | * | 11/1992 |
| EP | 0 228 539 | | 7/1987 |
| EP | 0 308 536 | | 3/1989 |
| JP | 2-30185 | * | 1/1990 |
| SU | 723 782 | | 3/1980 |

* cited by examiner

VOLTAGE-RESISTANT MOS SWITCH

CROSS-REFERENCE TO RELATED APPLICATIONS/INCORPORATION BY REFERENCE

This application claims priority to German patent application serial number 103 41 940.3 filed on Sep. 5, 2003.

This application also claims priority to German patent application serial number 103 58 048.4 filed on Dec. 5, 2003.

TECHNICAL FIELD

Embodiments of the present invention relate to metal-oxide semiconductor (MOS) devices. In particular, certain embodiments of the present invention concern a voltage-resistant switch comprising a first switching contact and a second switching contact, a first MOS switching transistor having a source terminal, a drain terminal and a gate terminal, wherein the source terminal of the first MOS switching transistor is connected to the second switching contact and the drain terminal of the first MOS switching transistor is connected to the first switching contact. The voltage-resistant switch is adapted for switching a potential which is to be applied to or which is applied to the first or second switching contact.

BACKGROUND OF THE INVENTION

In the case of MOS devices, the progressive reductions in size of structure and the smaller oxide thicknesses that this entails at the gate terminals gives rise to the problem that the supply voltage for modern circuits has to be further and further reduced. Excessively high supply voltages can lead to damage or even destruction of MOS devices, due to the change in electrical properties. Voltage resistance or dielectric strength in terms of the drain-source contacts in so-called high-voltage MOS transistors is achieved substantially by low-doped drift regions. In order not to worsen the electrical properties of the MOS transistors however the oxide thickness cannot be increased just by any desired amount to improve dielectric strength. In order to be able to transmit a voltage signal with an MOS transistor as far as possible without any influence, having regard to the threshold voltage of the MOS transistor, for example in the case of an NMOS transistor, the magnitude of the gate potential must be greater than the drain or source potential. In the case of multiplexers or output switches however it is often necessary to switch voltages which are higher than the technologically maximum admissible gate-source voltage. The problem also arises in relation to cardiac pacemakers or defibrillators in which stimulation or defibrillation signals which embrace a large dynamic range have to be switched. In that case the maximum admissible gate-source voltage can be exceeded, and that can result in damage to or destruction of the transistor.

DE 37 88 876 T2 discloses a programmable cardiac pacemaker which has MOS switches controllable by logic members. The problem of being able to switch only signals with signal voltages within a limited voltage range when using MOS switches is not mentioned here and is also not resolved.

SUMMARY OF THE INVENTION

Embodiments of the present invention provide a switch having MOS transistors, and having an elevated voltage resistance.

Various embodiments are attained by a voltage-resistant switch of the kind set forth in the opening part of this specification, wherein the voltage-resistant switch has a switching monitoring unit with a control input and a protection output. The voltage-resistant switch also has a protection switch having a switching input connected to the protection output of the switching monitoring unit. The protection switch is arranged and adapted to electrically connect the gate terminal of the first MOS switching transistor to the source terminal of the first MOS switching transistor in dependence on a protection signal so that the gate terminal and the source terminal of the first MOS switching transistor can be connected together by way of a sufficiently low resistance.

The switching monitoring unit is adapted to produce a corresponding protection signal for putting the protection switch into its switching condition of connecting the gate and source terminals of the first MOS switching transistor and outputting same at the protection output when the first MOS switching transistor is non-conducting. That prevents overloading of the gate-source path of the first MOS switching transistor in the non-conducting condition thereof.

In this embodiment, the voltage-resistant switch has precisely one MOS switching transistor which is referred to here as the first MOS switching transistor.

In a variant embodiment, the protection switch is an MOS protection transistor whose switching input is formed by a gate terminal. The drain terminal of the first MOS protection transistor is connected to the gate terminal of the first MOS switching transistor and the source terminal of the first MOS protection transistor is connected to the source terminal of the first MOS switching transistor.

In this variant embodiment, the switching monitoring unit is adapted, in the non-conducting condition of the first MOS switching transistor, to act on the gate terminal of the first MOS protection transistor with a switching-through potential in such a way that the first MOS protection transistor is caused to conduct and, in the situation where the first MOS switching transistor is in a conducting condition, to act on the gate terminal of the first MOS protection transistor with a blocking potential such that the first MOS protection transistor is non-conducting.

In another variant embodiment, the switching monitoring unit is adapted, when a predetermined potential difference is exceeded between the source terminal and the gate terminal of the first MOS switching transistor or between the first switching contact and the second switching contact, to act on the gate terminal of the first MOS protection transistor with a switching-through potential, in such a way that the first MOS protection transistor is, ideally completely but not necessarily completely, caused to conduct and when the potential difference falls below a predetermined potential difference between the first switching contact and the second switching contact of the voltage-resistant switch or in a situation where the switching transistor is caused to conduct, to act on the gate terminal of the first MOS protection transistor with a blocking potential in such a way that the first MOS protection transistor is, ideally completely but not necessarily completely, non-conducting.

That circuit arrangement for a voltage-resistant switch provides that, in the non-conducting condition, the gate terminal and the source terminal of the switching transistor are short-circuited. That advantageously avoids the maximum admissible voltage being exceeded, which in the non-conducting condition may be dropped between the source contact and the gate contact of the switching transistor. It is, therefore, a feature of the invention that the voltage-resistant switch can be operated at higher potential differences between the switching contacts than the voltage resistance of the individual switching transistors allows without the switching transistors suffering damage.

Irrespective of whether the voltage-resistant switch has a protection switch of the kind described hereinbefore, and irrespective of whether the switching monitoring unit has a corresponding protection output, the switching monitoring unit can have a control output connected to the gate terminal of the MOS switching transistor. The switching monitoring unit is adapted to act on the gate terminal of the first MOS switching transistor with such a control potential which causes conduction or non-conduction, in particular complete conduction or complete non-conduction, of the first MOS switching transistor between the source terminal and the drain terminal.

For that purpose, the switching monitoring unit can be at least indirectly connected at its input side to the first switching contact and the second switching contact. In that way the switching monitoring unit can detect a potential at a switching contact.

The switching monitoring unit is preferably adapted to select the control potential from a number of predetermined control potentials in dependence on a predetermined switching potential or a first potential to be applied to or applied to the first switching contact, or a second potential to be applied to or applied to the second switching contact, or both in a predetermined manner, more specifically from a number of predetermined control potentials in accordance with a predetermined allocation specification.

Embodiments by way of example of a circuitry implementation of an allocation specification can be networks with an input and an output, including passive and/or active components, which have a transfer function, representing the allocation specification, between an output and an input.

In another embodiment of the present invention, the predetermined potentials, which are applied to or which are to be applied to the first and/or the second switching contact and the associated switching potentials, are embodied in a look-up table or in the form of a control program.

An example of a preferred allocation specification for a gate potential which is to be selected in dependence on a potential to be applied to a switching contact is illustrated in the Table hereinafter:

| Ux [V] | UG [V] |
|---|---|
| 0 | U |
| −U | U |
| −U | 0 |
| −2*U | 0 |
| −2*U | −U |
| −3*U | −U |

In the foregoing Table, the potentials which are to be applied to or are applied to a switching contact are identified as Ux and the respectively corresponding gate potentials for switching are identified as UG, in each case in relation to a common reference node. The voltage U specified in the Table can be a voltage which is predetermined in an apparatus. It is also possible to envisage positive potentials which are to be applied to or are applied to a switching contact.

As an alternative thereto, the switching monitoring unit can be adapted to select the control potential from a number of predetermined control potentials, in such a way that the control potential is in a predetermined relationship with a first potential which is applied to or is to be applied to the first switching contact and a second potential which is applied to or is to be applied to the second switching contact.

The above-described configurations advantageously provide that the MOS switching transistor can be operated in the triode range and no signal distortions occur which would appear in operation of the MOS switching transistor above the pinch-off operating point.

In another variant embodiment, the voltage-resistant switch has a second MOS switching transistor. The second MOS switching transistor is connected in series with the first MOS switching transistor in such a way that the source terminal of the second MOS switching transistor is connected, ideally directly but not necessarily directly, to the source terminal of the first MOS switching transistor and the drain terminal of the first MOS switching transistor is connected, ideally directly but not necessarily directly, to the first switching contact and the drain terminal of the second MOS switching transistor is connected, ideally directly but not necessarily directly, to the second switching contact.

In a further embodiment of the present invention, the gate terminal of the first switching transistor is connected, ideally directly but not necessarily directly, to the gate terminal of the second MOS switching transistor.

As an alternative thereto, the gate terminal of the second switching transistor can also be connected to the switching monitoring unit which in that case is adapted, in dependence on a potential which is to be applied to or which is applied to the first switching contact and/or a potential which is to be applied to or which is applied to the second switching contact, to act on the gate terminals of the switching transistors independently of each other respectively with a control potential which is predetermined for the respective switching transistor.

In a further embodiment of the present invention, the switching monitoring unit has a center potential terminal connected to the source terminals of the switching transistors, wherein the switching monitoring unit is adapted, when the switching transistors are in the non-conducting condition, to act on the center potential terminal with a center potential such that a respective predetermined potential difference is not exceeded between the center potential terminal and the gate terminals of the switching transistors. The predetermined potential difference is, ideally but not necessarily, less than the maximum admissible gate-source voltage of the switching transistors. A particular potential difference is 0 volt, for example.

In the case of an arrangement having two switching transistors, a voltage applied to the first switching contact and to the second switching contact is dropped across the first switching transistor and the second switching transistor so that, in that arrangement, the demands on a switching transistor in terms of voltage resistance are lower. In that arrangement the switching transistors conduct at the same time or are non-conducting jointly.

In a further embodiment of the present invention, the voltage-resistant switch has a second MOS protection transistor which is connected in series with the first MOS protection transistor in such a way that the source terminal of the second MOS protection transistor is connected, ideally directly but not necessarily directly, to the source terminal of the first MOS protection transistor so that the drain terminal of the second MOS protection transistor is connected, ideally directly but not necessarily directly, to the source terminal of the first MOS switching transistor and the drain terminal of the first MOS protection transistor is connected, ideally directly but not necessarily directly, to the gate terminal of the first MOS switching transistor and optionally also a second MOS switching transistor and the gate terminal of the first MOS protection transistor is connected, ideally directly but not necessarily directly, to the gate terminal of the second MOS protection transistor. In this arrangement, the protection transistors conduct at the same time or are non-conducting jointly. That advantageously implements non-conduction of the protection transistors irrespective of the potential direction.

The gate terminals of the two MOS protection transistors can also be actuated with differing potentials in alternative variants in which the two gate terminals are not directly connected together.

In a certain embodiment, each MOS switching transistor has a bulk terminal which is connected to the source terminal of the respective MOS switching transistor. In that way, a greater current can advantageously flow on the source-drain path of each switching transistor.

In a further embodiment, each MOS protection transistor has a bulk terminal which is connected to the source terminal of the respective MOS protection transistor. By virtue of that arrangement, in the case of a low-ohmic connection of the gate terminal and the source terminal of the switching transistor, an elevated short-circuit current can flow through the protection transistors.

In a variant embodiment, the MOS switching transistors and the MOS protection transistors are in the form of asymmetrical MOS transistors. The voltage-resistant switch is thus of a symmetrical configuration with respect to the switching contacts and operates independently of the polarity of the voltage which is applied across the switching contacts.

In an alternative embodiment, the MOS switching transistors and the MOS protection transistors are in the form of insulated gate bipolar transistors. In this embodiment, the voltage-resistant switch can advantageously switch high voltages and large currents.

In a particular embodiment, the voltage-resistant switch is monolithically integrated. In this embodiment the voltage-resistant switch is advantageously integrated in a unit.

Ideally but not necessarily, the MOS transistors of the voltage-resistant switch are in the form of NMOS transistors, further in the form of self-blocking NMOS transistors. The MOS transistors can also be in the form of PMOS transistors, further in the form of self-blocking PMOS transistors. It is also possible to envisage an embodiment in which the protection transistors are in the form of self-conducting MOS transistors.

Certain embodiments of the present invention also concern a cardiac pacemaker or a defibrillator with the voltage-resistant switch. A voltage-resistant switch, in accordance with one of the above-indicated embodiments, can be used in a particularly advantageous fashion in a cardiac pacemaker or a defibrillator in which the voltage and the polarity of a stimulation pulse to be switched is variable.

A stimulation unit for the stimulation of a heart can advantageously have a voltage-resistant switch, according to an embodiment of the present invention, and a capacitor for storage of electrical charge for a stimulation signal. In that case, the voltage-resistant switch is operatively connected to the capacitor in such a way that discharge of the capacitor can take place by way of the voltage-resistant switch. The stimulation unit can be a component part of an apparatus for the stimulation of a heart, for example, a cardiac pacemaker or a defibrillator.

The stimulation unit advantageously includes a control unit which is connected to the voltage-resistant switch and adapted to switch stimulation signals for stimulating a heart with the voltage-resistant switch. In that respect, the control unit can be adapted to switch a stimulation signal to a stimulation electrode by way of the voltage-resistant switch.

DETAILED DESCRIPTION OF THE INVENTION

Figure 1:
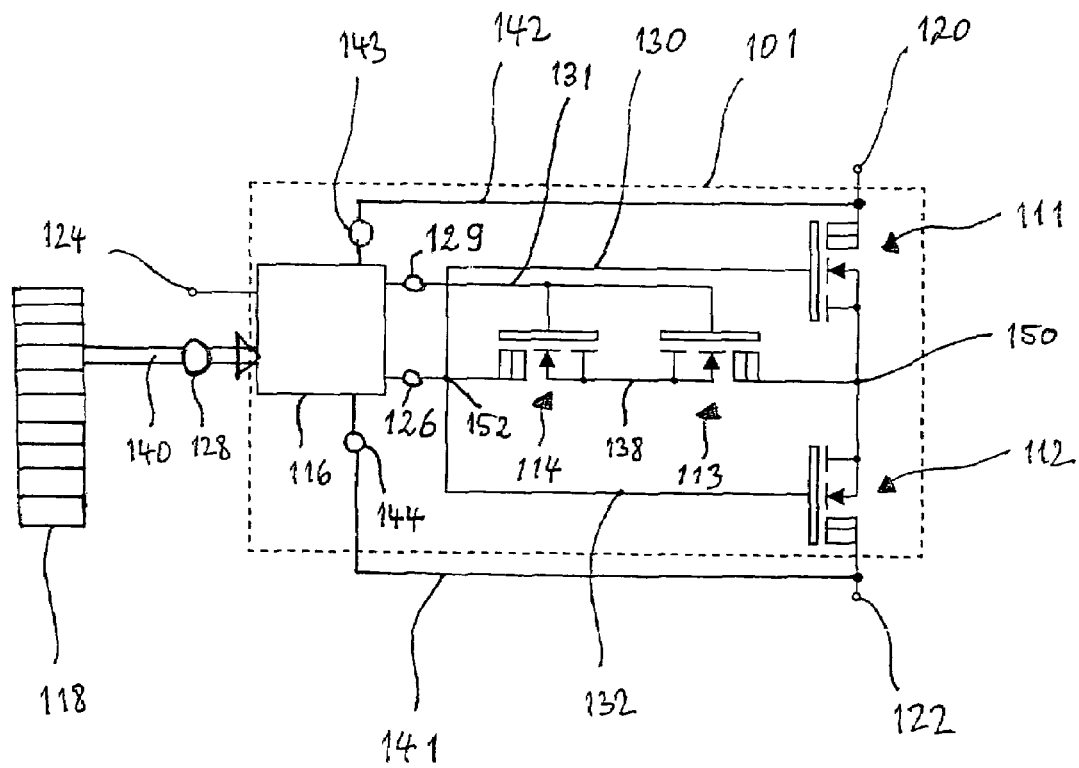
FIG. 1 diagrammatically shows an embodiment of a circuit arrangement of a voltage-resistant switch with MOS transistors, in accordance with various aspects of the present invention.

FIG. 1 diagrammatically shows an embodiment of a circuit arrangement of a voltage-resistant switch with MOS transistors, in accordance with various aspects of the present invention. Referring to FIG. 1, diagrammatically shown therein is a circuit arrangement for a voltage-resistant MOS switch 101.

The voltage-resistant switch 101 includes a first switching contact 120, a second switching contact 122, a first MOS switching transistor 111 and a second MOS switching transistor 112, the source terminals of which are connected together by way of a node 150. The drain terminal of the first switching transistor 111 is connected to the first switching contact 120 and the drain terminal of the second switching transistor 112 is connected to the second switching contact 122. The MOS switching transistors 111 and 112 in the an embodiment are in the form of asymmetrical MOS transistors but can also be of a symmetrical configuration for given uses. For that purpose the doping of the source regions is different in comparison with the drain regions. In each MOS switching transistor, the source terminal is connected to the bulk terminal. In this arrangement, the switching transistors are of a symmetrical arrangement in respect of the switching contacts 120 and 122 so that the switch can operate independently of the polarity of a signal to be switched.

The voltage-resistant switch 101 has a switching monitoring unit 116 with a control input 124, a control output 126, and a protection output 129. The control output 126 is connected by way of a node 152 and connecting lines 130 and 132 to the gate terminal of the first switching transistor 111 and to the gate terminal of the second switching transistor 112. The voltage-resistant switch 101 also has a first MOS protection transistor 114 and a second MOS protection transistor 113, the source terminals of which are connected together by way of a connecting line 138 and the gate terminals of which are connected by way of a connecting line 131 to the protection output 129 of the switching monitoring unit 116. The drain terminal of the first MOS protection transistor 114 is connected to the node 152 and the drain terminal of the second MOS protection transistor 113 is connected to the node 150. The MOS protection transistors 113 and 114 are in the form of asymmetrical MOS transistors and the source terminal of each MOS protection transistor is connected to the respective bulk terminal.

The switching monitoring unit 116 has a potential output 128 connected by way of a data bus 140 to a memory array 118. The memory array 118 contains discrete potential levels which the switching monitoring unit 116 can selectively access by way of the databus 140. The switching monitoring unit 116 has a first potential input 143 which is connected to the first switching contact 120 by way of a first contact potential line 142, and a second potential input 144 which is connected to the second switching contact 122 by way of a second contact potential line 141. The switching monitoring unit is adapted, optionally in dependence on predetermined potentials at the first switching contact 120 and/or the second switching contact 122, to produce a switching-through potential or a blocking potential for the protection transistors and to act on the protection output 129 with the switching-through potential or the blocking potential so that, when the switching transistors are in the non-conducting condition, the switching-through potential of the protection transistors is so set that the source and gate terminals of the switching transistors 111 and 112 are connected in low-ohmic relationship by way of the MOS protection transistors 113 and 114.

As a result, the switching transistors 111, 112 are protected in the event of blocking thereof if the protection output 129 is acted upon with a switching-through potential. In the circuitry illustrated in FIG. 1 the MOS transistors are in the form of self-blocking NMOS transistors.

As an alternative to the configuration in the form of self-blocking MOS transistors, the protection transistors 113 and 114 can also be in the form of self-conducting MOS transistors. In that case, the switching monitoring unit 116 is adapted to act on the protection output 129 with a blocking potential if the source and gate terminals of the switching transistors 111 and 112 are not to be short-circuited.

The mode of operation of the voltage-resistant switch will now be described hereinafter:

If a control signal for causing the voltage-resistant MOS switch 101 to conduct is applied at the control input 124, the switching monitoring unit produces a switching-through potential and acts therewith on the control output 126 and the connected gate terminals of the MOS switching transistors 111 and 112. The switching monitoring unit is adapted to select the control potential from a number of predetermined control potentials in dependence on a first potential which is to be applied to the first switching contact, or a second potential which is to be applied to the second switching contact or both in accordance with an allocation specification so that the operating points of the MOS switching transistors are in the triode range below the pinch-off operating point. The predetermined control potentials are stored in the memory array 118 and are available in digital form as discrete potential values by way of the databus 140.

An example of the potentials stored in the memory array is illustrated in the Table hereinafter, the respective corresponding values of which represent an allocation specification:

| Ux | UG |
|---|---|
| 0 V | 2.8 V |
| −2.8 V | 2.8 V |
| −2.8 V | 0 V |
| −5.6 V | 0 V |
| −5.6 V | −2.8 V |
| −8.4 V | −2.8 V |

In the Table hereinbefore, the voltages which are to be applied to or are applied to a switching contact are identified as Ux and the respectively corresponding gate potentials for switching purposes are identified as UG, in each case in relation to a common reference node.

As an alternative thereto, it is also possible to envisage an analog variant, in which case the memory array contains analog signals and the data bus 140 has a connecting line for each control potential. If a control signal is applied at the control input 124 for blocking the voltage-resistant MOS switch 101, the switching monitoring unit produces a blocking potential and acts therewith on the control output and the connected gate terminals of the MOS switching transistors 111 and 112. If, when the switching transistors 111 and 112 are in the non-conducting condition the potential difference between the switching contacts 120 and 122 exceeds a predetermined voltage value, then the switching monitoring unit 116 produces a switching-through potential and acts therewith on the protection output 129, and thus the gate terminals, which are connected thereto by way of the connecting line 136, of the protection transistors 113 and 114 so that the protection transistors 113 and 114 are in the completely conducting condition. In that situation, a predetermined potential difference between the switching contacts 120 and 122 in the non-conducting condition can correspond to a potential difference between the source terminal and the gate terminal of a switching transistor.

The switching monitoring unit 116 can also be adapted, when the switching transistors 111, 112 are in the non-conducting condition, to produce a switching-through potential to prevent a predetermined potential difference being exceeded between the source terminal and the gate terminal of a switching transistor, at the protection output.

As a result, the source and gate terminals of the switching transistors 111 and 112 are connected together in low-resistance relationship so that a voltage which is dropped in the non-conducting condition of the voltage-resistant switch across those terminals is short-circuited and the MOS switching transistors 111 and 112 cannot be damaged.

In an alternative embodiment (not shown), the contact potential lines 141 and 142 are omitted. In this embodiment, the potential inputs 143 and 144 can each be supplied with a potential signal corresponding to an actual potential at the respective switching contacts so that galvanic separation is implemented between the switching contacts and the potential inputs 143 and 144.

Figure 2:
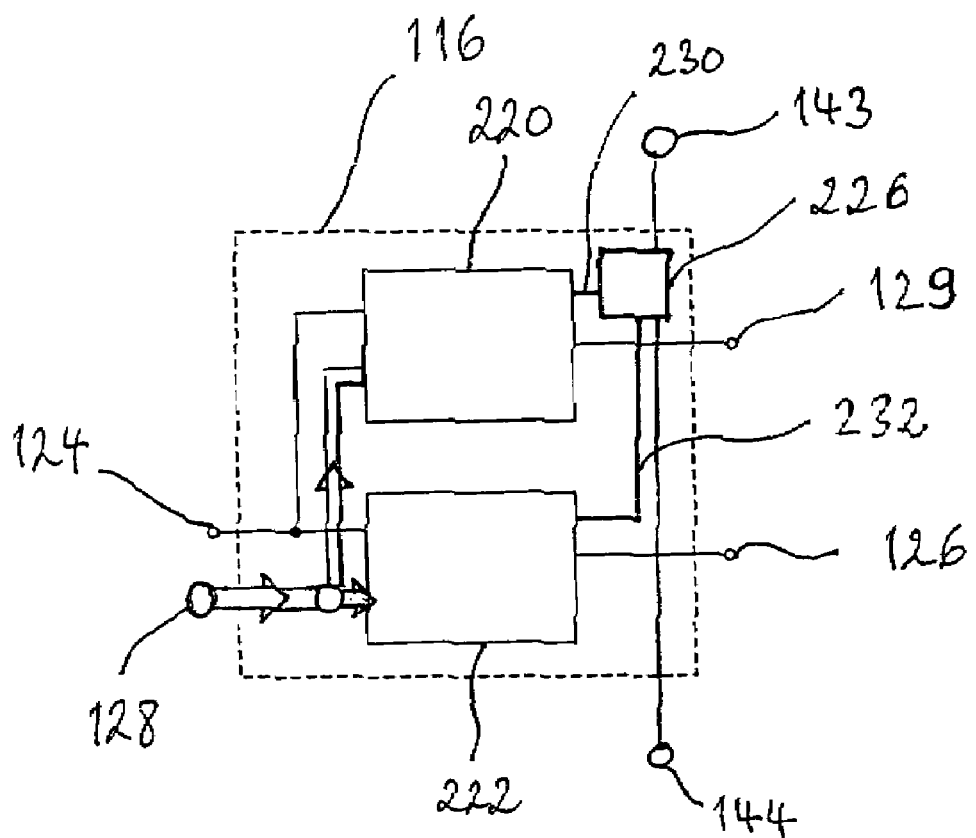
FIG. 2 is a diagrammatic view of an embodiment of a switching monitoring unit with two voltage generators for a voltage-resistant switch, in accordance with various aspects of the present invention.

FIG. 2 is a diagrammatic view of an embodiment of a switching monitoring unit with two voltage generators for a voltage-resistant switch, in accordance with various aspects of the present invention.

As FIG. 2 shows, the switching monitoring unit includes two monitoring units 220 and 222 and a control unit 226. The allocation specification which is relevant for use of the voltage-resistant switch 101, between the gate voltage to be applied in relation to a drain-source voltage which is to be switched through, is established in the control unit 226, for example, in terms of circuitry or in a look-up table.

The monitoring unit 222 is adapted to produce, from a control signal at the control input 124 and the discrete potential levels made available by the memory array 118, a corresponding discrete gate signal for the transfer transistors 111 and 112 in FIG. 1, in accordance with the allocation specification established in the control unit 226. For that purpose, the control unit 226 is adapted to produce an allocation signal in dependence on the potentials obtaining at the switching contacts 120 and 122, in accordance with the allocation specification, and to send that allocation signal to the monitoring unit 222 by way of an output and a connecting line 232. For that purpose, the control unit 226 has a first potential input 143 which is connected to the first switching contact and a second potential input 144 which is connected to the second switching contact 122.

The monitoring unit 220 is adapted, depending on the respective operating point of the switching transistors 111 and 112, to produce a switching-through potential or a blocking potential and, in the non-conducting condition, by suitable actuation of the protection transistors 113 and 114, to form a low-resistance connection between the gate and source terminals of the switching transistors 111 and 112. The control unit 226 is adapted to produce a protection signal representative of the switching-through potential or the blocking potential in accordance with an allocation specification in dependence on the potentials at the potential inputs 143 and 144 and to send the protection signal by way of an output and a connecting line 230 to the monitoring unit 220. The monitoring unit is adapted to produce, from a control signal at the control input 124 and the discrete voltage levels made available by the memory array 118, a corresponding discrete gate signal for the protection transistors 113 and 114 in FIG. 1, in accordance with the protection signal and thus also in accordance with the allocation specification established in the control unit 226, and to act on the protection output 129 with a discrete switching-through potential or a discrete blocking potential.

Figure 3:
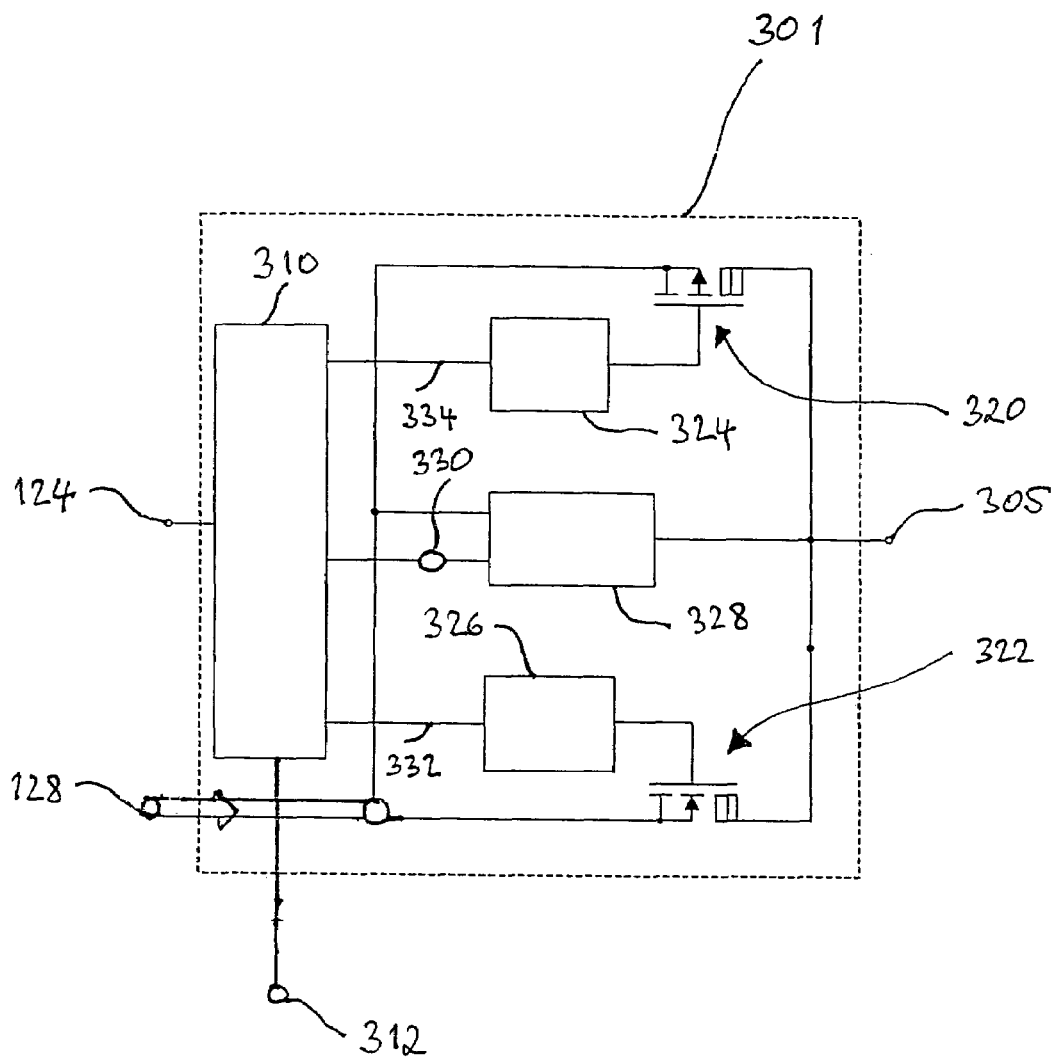
FIG. 3 is a diagrammatic view of an embodiment of a voltage generator for a switching monitoring unit, in accordance with various aspects of the present invention.

FIG. 3 is a diagrammatic view of an embodiment of a voltage generator for a switching monitoring unit, in accordance with various aspects of the present invention. FIG. 3 shows a possible monitoring circuit 301 for the monitoring units 220 and 222.

The monitoring circuit 301 includes a selection unit 310 with a control input 124 and an allocation input 312 for the protection signal or the allocation signal, the allocation input 312 being connected to the control unit 226. For each potential level stored in the memory array the monitoring circuit includes a level shifter and a transfer transistor connected thereto for producing the potential corresponding to that potential level. A transfer transistor and a level shifter connected thereto form a transfer unit.

The discrete potential levels made available by the memory array 118—in this embodiment in analog form—are switched according to the respective drain-source voltage to be switched through by way of transfer transistors 320 and 322 to the node 305 which, in the case of the monitoring unit 220, is connected to the protection output 129 or, in the case of the monitoring unit 222, to the control output 126. The transfer transistors 320 and 322 are in turn actuated by way of the appropriate digital level shifters 324 and 326. The further potential levels are switched by way of corresponding transfer units (not shown in this embodiment) to the node 305. The level shifters 324 and 326 each have a respective actuation input 332 or 334 connected to the selection unit 310. Depending on which potential level is actuated by way of the protection signal or allocation signal at the allocation input 312, the selection unit 310 actuates the transfer unit which is connected thereto and which corresponds to the respective potential level. The selection unit 310 thus provides that only one of the potential levels which are stored in the memory array 118, that potential level corresponding to the allocation signal or the protection signal, is converted by way of the transfer units into a corresponding potential and switched by the transfer unit to the node 305. FIG. 3 also illustrates a transfer unit 328 which, like the transfer units already described above, can include a level shifter and a transfer transistor connected thereto.

Independently of the analog variant described hereinbefore, it is also possible to conceive of an alternative configuration with only one D/A transfer unit instead of the transfer unit 328 which is in the form of a D/A potential converter. This alternative configuration no longer has the illustrated transfer units which include the level shifters 324 and 326 and the transfer transistors 320 and 322. The transfer unit 328 is adapted, by way of the actuation input 330 connected to the selection unit 310, to receive a digital potential level formed by the selection unit 310—corresponding to the allocation or protection signal using a discrete potential level—and to form a corresponding analog potential and apply it to the node 305. The selection unit 310 in this embodiment is adapted to associate a continuous potential value at the allocation input 310 with a discrete potential level and produce a corresponding output signal. The continuous potential value is represented by the allocation signal or the protection signal.

The components shown in FIGS. 1, 2 and 3 can be monolithically embodied on an integrated circuit, in accordance with various embodiments of the present invention.

Figure 4:
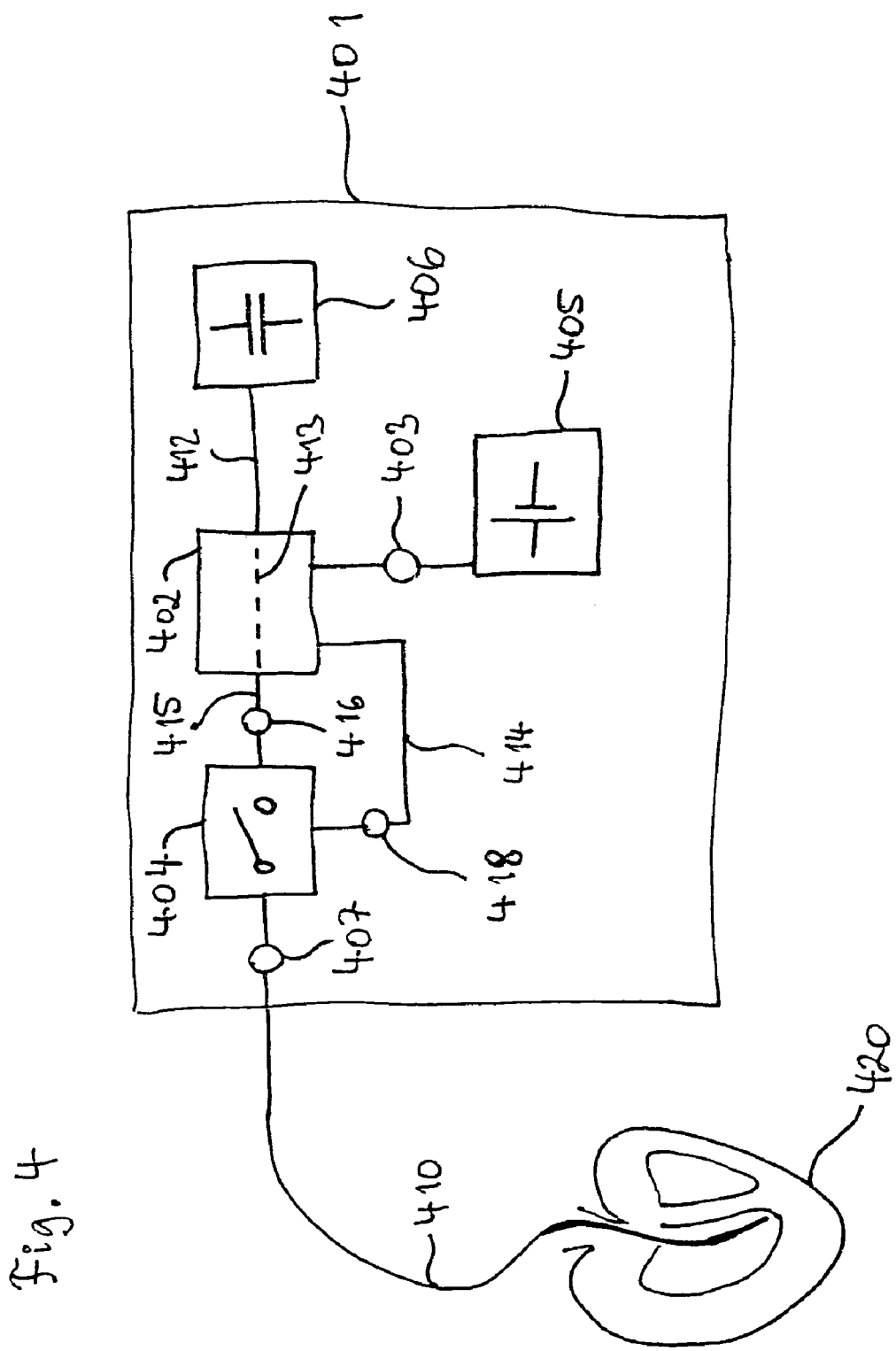
FIG. 4 diagrammatically shows an embodiment of a stimulation unit with a voltage-resistant switch for the stimulation of a heart, in accordance with various aspects of the present invention.

FIG. 4 diagrammatically shows an embodiment of a stimulation unit 401 with a voltage-resistant switch for the stimulation of a heart 420, in accordance with various aspects of the present invention. The stimulation unit 401 includes a control unit 402 connected by way of a connecting line 412 to a capacitor 406 for storing stimulation energy in the form of an electrical charge. The control unit 402 is connected by way of a control line 414 to a control input 418 and by way of a stimulation pulse line 415 to a first switching contact 416 of a voltage-resistant switch 404. A second switching contact 407 of the voltage-resistant switch 404 forms a stimulation output to which a stimulation electrode can be connected. The control unit 402 has a current supply input 403 for the connection of a battery 405. The control unit 402 is adapted to control charging and discharging of the capacitor 406 to provide stimulation energy.

In a simple embodiment, the control unit 402 is adapted to control the discharging process of the capacitor 406 by way of the voltage-resistance switch 404. For that purpose, the control unit 402 can produce a control signal and switch it by way of the control line 414 to the control input 418 of the voltage-resistant switch 404. In this embodiment, the connecting line 412 is connected to the stimulation pulse line 415 by way of a bridge line 413 shown in broken line.

In another embodiment, a pulse-shaping control unit instead of the control unit 402 can produce a defibrillation or stimulation pulse with the stimulation energy from the capacitor 406 and switch that pulse by way of the voltage-resistant switch 404 to a stimulation output 407 and thus to a stimulation electrode 410 connected thereto. In this embodiment, the stimulation pulse is different from an R-C-discharging function and can be, for example, patient-specifically adapted. This embodiment does not involve the bridge line 413.

What is claimed is:

1. A voltage-resistant switch, said switch comprising:
    a first switching contact;
    a second switching contact;
    a first MOS switching transistor having a source terminal, a drain terminal, and a gate terminal, and wherein the source terminal of the first MOS switching transistor is connected to the second switching contact, and the drain terminal of the first MOS switching transistor is connected to the first switching contact, and wherein the voltage-switch is adapted for switching a potential which is to be applied to or which is applied to the first or the second switching contact; and
    a switching monitoring unit with a control input and a protection output which is connected to a switching input of a protection switch, and wherein said protection switch electrically connects the gate terminal of the first MOS switching transistor to the source terminal of the first MOS switching transistor in dependence on a protection signal when the switching monitoring unit outputs the protection signal to a protection input of the protection switch, and wherein the switching monitoring unit is adapted to produce and output said protection signal in dependence on a potential at either said gate terminal or said source terminal of said first MOS switching transistor to provide protection against exceeding a breakdown voltage of said first MOS switching transistor, wherein the switching monitoring unit includes a control output connected to the gate terminal of the first MOS switching transistor, and wherein the switching monitoring unit is adapted for acting on the gate terminal of the first MOS switching transistor with a control potential for turning on or for blocking the first MOS switching transistor, between the source terminal and the gate terminal of the first MOS switching transistor, and wherein the switching monitoring unit is adapted to select the control potential from a number of predetermined control potentials in dependence on a predetermined switching potential that is to be switched by said voltage-resistant switch, or a first potential which is applied to or is to be applied to the first switching contact and is to be switched by said voltage-resistant switch and/or a second potential which is applied to or is to be applied to the second switching contact and is to be switched by said voltage-resistant switch, in a predetermined manner.

2. The voltage-resistant switch of claim 1 wherein the protection switch includes a first MOS protection transistor having a switching input formed by a gate terminal, and wherein a drain terminal of the first MOS protection transistor is connected to the gate terminal of the first MOS switching transistor, and a source terminal of the first MOS protection transistor is connected to the source terminal of the first MOS switching transistor, and wherein the switching monitoring unit is adapted, in a blocking condition of the first MOS switching transistor, to act on the gate terminal of the first MOS protection transistor with a switching-through potential such that the first MOS protection transistor turns on and, when the first MOS switching transistor is turned on, to act on the gate terminal of the first MOS protection transistor with a blocking potential such that the first MOS protection transistor blocks.

3. The voltage-resistant switch of claim 2 further comprising a second MOS switching transistor being connected in series with the first MOS switching transistor such that a source terminal of the second MOS switching transistor is connected to the source terminal of the first MOS switching transistor, and the drain terminal of the first MOS switching transistor is connected to the first switching contact, and a drain terminal of the second MOS switching transistor is connected to the second switching contact.

4. The voltage-resistant switch of claim 3 wherein a gate terminal of the second MOS switching transistor is connected separately to the switching monitoring unit and the switching monitoring unit is adapted, in dependence on a potential which is to be applied to or is applied to the first switching contact and/or a potential which is to be applied to or is applied to the second switching contact, to act on the gate terminals of the MOS switching transistors respectively, independently of each other with a control potential which is predetermined for the respective MOS switching transistors.

5. The voltage-resistant switch of claim 4 wherein the switching monitoring unit includes a center potential terminal connected to the source terminals of the MOS switching transistors, and wherein the switching monitoring unit is adapted, upon blocking of the MOS switching transistors, to act on the center potential terminal with a center potential such that a respective predetermined potential difference between the center potential terminal and the gate terminals of the MOS switching transistors is not exceeded.

6. The voltage-resistant switch of claim 5 wherein the gate terminal of the first MOS switching transistor is connected to a gate terminal of the second MOS switching transistor.

7. The voltage-resistant switch of claim 6 further comprising a second MOS protection transistor is connected to the source terminal at least of the first MOS switching transistor, and the drain terminal of the first MOS protection transistor is connected to the gate terminal at least of the first MOS switching transistor, and the gate terminal of the first MOS protection transistor is connected to a gate terminal of the second MOS protection transistor.

8. The voltage-resistant switch of claim 7 wherein each MOS switching transistor includes a bulk terminal, the bulk terminal being connected to the respective source terminal.

9. The voltage resistant switch of claim 8 wherein each MOS protection transistor includes a bulk terminal, the bulk terminal being connected to the respective source terminal.

10. The voltage-resistant switch of claim 9 wherein the MOS switching transistors and the MOS protection transistors are in the form of asymmetrical MOS transistors.

11. The voltage-resistant switch of claim 10 wherein the MOS switching transistors and the MOS protection transistors are in the form of insulated gate bipolar transistors.

12. The voltage-resistant switch of claim 11 wherein the voltage-resistant switch is monolithically integrated.

13. A cardiac pacemaker or defibrillator, said cardiac pacemaker or defibrillator comprising a voltage-resistant switch wherein said voltage-resistant switch includes a first switching contact, a second switching contact, and a first MOS switching transistor having a source terminal, a drain terminal, and a gate terminal wherein the source terminal of the first MOS switching transistor is connected to the second switching contact, and the drain terminal of the first MOS switching transistor is connected to the first switching contact, and wherein the voltage-resistant switch is adapted for switching a potential which is to be applied to or which is applied to the first or the second switching contact, and wherein the voltage-resistant switch also includes a switching monitoring unit with a control input and a protection output which is connected to a switching input of a protection switch, and wherein said protection switch electrically connects the gate terminal of the first MOS switching transistor to the source terminal of the first MOS switching transistor in dependence on a protection signal when the switching monitoring unit outputs the protection signal to a protection input of the protection switch, and wherein the switching monitoring unit is adapted to produce and output said protection signal in dependence on a potential at either said gate terminal or said source terminal of said first MOS switching transistor to provide protection against exceeding a breakdown voltage of said first MOS switching transistor, wherein the switching monitoring unit includes a control output connected to the gate terminal of the first MOS switching transistor, and wherein the switching monitoring unit is adapted for acting on the gate terminal of the first MOS switching transistor with a control potential for turning on or for blocking the first MOS switching transistor, between the source terminal and the gate terminal of the first MOS switching transistor, and wherein the switching monitoring unit is adapted to select the control potential from a number of predetermined control potentials in dependence on a predetermined switching potential that is to be switched by said voltage-resistant switch, or a first potential which is applied to or is to be applied to the first switching contact and is to be switched by said voltage-resistant switch and/or a second potential which is applied to or is to be applied to the second switching contact and is to be switched by said voltage-resistant switch, in a predetermined manner.

14. A stimulation unit for the stimulation of a heart, said stimulation unit comprising:

a capacitor for the storage of electrical charge for a stimulation signal; and a voltage-resistant switch including a first switching contact, a second switching contact, and a first MOS switching transistor having a source terminal, a drain terminal, and a gate terminal wherein the source terminal of the first MOS switching transistor is connected to the second switching contact, and the drain terminal of the first MOS switching transistor is connected to the first switching contact, and wherein the voltage-resistant switch is adapted for switching a potential which is to be applied to or which is applied to the first or the second switching contact, and wherein the voltage-resistant switch also includes a switching monitoring unit with a control input and a protection output which is connected to a switching input of a protection switch, and wherein said protection switch electrically connects the gate terminal of the first MOS switching transistor to the source terminal of the first MOS switching transistor in dependence on a protection signal when the switching monitoring unit outputs the protection signal to a protection input of the protection switch, and wherein the switching monitoring unit is adapted to produce and output said protection signal in dependence on a potential at either said gate terminal or said source terminal of said first MOS switching transistor to provide protection against exceeding a breakdown voltage of said first MOS switching transistor, and wherein the voltage-resistant switch is operatively connected to the capacitor such that discharging of the capacitor takes place by way of the voltage-resistant switch, wherein the switching monitoring unit includes a control output connected to the gate terminal of the first MOS switching transistor, and wherein the switching monitoring unit is adapted for acting on the gate terminal of the first MOS switching transistor with a control potential for turning on or for blocking the first MOS switching transistor, between the source terminal and the gate terminal of the first MOS switching transistor, and wherein the switching monitoring unit is adapted to select the control potential from a number of predetermined control potentials in dependence on a predetermined switching potential that is to be switched by said voltage-resistant switch, or a first potential which is applied to or is to be applied to the first switching contact and is to be switched by said voltage-resistant switch and/or a second potential which is applied to or is to be applied to the second switching contact and is to be switched by said voltage-resistant switch, in a predetermined manner.

15. The stimulation unit of claim 14 further comprising a control unit, wherein the control unit is connected to the voltage-resistant switch and is adapted to switch stimulation ignals, for the stimulation of a heart, with the voltage-resistant switch.

* * * * *

UNITED STATES PATENT AND TRADEMARK OFFICE
CERTIFICATE OF CORRECTION

PATENT NO.        : 7,599,159 B2
APPLICATION NO.   : 10/933816
DATED             : October 6, 2009
INVENTOR(S)       : Ulrich Feese, Robert Kessler and Michael Wrana It is certified that error appears in the above-identified patent and that said Letters Patent is hereby corrected as shown below:

Claim 1, column 10, line 63 - replace "voltage-switch" with "voltage-resistant switch"

Claim 5, column 12, line 10 - replace "tenninal" with "terminal"

Claim 7, column 12, line 16 - insert --which is connected in series with the first MOS protection transistor such that a source terminal of the second MOS protection transistor is connected to the source terminal of the first MOS protection transistor, and a drain terminal of the second MOS protection transistor-- before "is connected to the"

Claim 15, column 14, line 34 - replace "ignals" with "signals"

Signed and Sealed this

Twenty-fourth Day of November, 2009

David J. Kappos
*Director of the United States Patent and Trademark Office*